United States Patent [19]

Narumiya et al.

[11] Patent Number: 4,812,457

[45] Date of Patent: Mar. 14, 1989

[54] PROSTAGLANDIN DERIVATIVES

[75] Inventors: Shuh Narumiya; Osamu Hayaishi, both of Kyoto; Yoshiharu Kimura, Omihachiman; Masami Tsuboshima, 13-2, Nakasajijo-cho, Ibaraki-shi, Osaka-fu, Japan

[73] Assignees: Research Development Corporation, Osaka; Masami Tsuboshima, Tokyo, both of Japan

[21] Appl. No.: 149,930

[22] Filed: Jan. 29, 1988

Related U.S. Application Data

[63] Continuation of Ser. No. 793,826, Nov. 1, 1985, abandoned.

[30] Foreign Application Priority Data

Nov. 21, 1984 [JP] Japan .................................. 59-247241

[51] Int. Cl.$^4$ .................. C07C 177/00; A61K 31/557
[52] U.S. Cl. ................................ 514/226.2; 514/389; 514/452; 514/530; 544/39; 548/313; 549/363; 560/119; 560/121
[58] Field of Search .................. 560/121, 119; 544/39; 548/313; 549/363; 514/225, 530, 452, 389

[56] References Cited

FOREIGN PATENT DOCUMENTS

| 25687 | 3/1981 | European Pat. Off. ............ 560/121 |
| 30299 | 6/1981 | European Pat. Off. ............ 560/121 |
| 144069A | 6/1985 | European Pat. Off. ............. 560/12 |

OTHER PUBLICATIONS

Kirk-Othmer, Encyclopedia of Chemical Technology, 3rd Ed., Supplement vol. 1984, pp. 711-752.
Chem. Abstr., vol. 96, No. 19, p. 178, abstract No. 156368u, 5/82.
Chem. Abstr. vol. 97. No. 7, p. 252, abstract No. 51485x, 8/82.
Hatsumi, J of Chrom. 253, 271 (1982).

Primary Examiner—Robert Gerstl

[57] ABSTRACT

Permeability characterized in that the carboxy group at 1-position of the prostaglandin is combined with a cell membrane permeable substance having hydroxy group or amino group through the intermediation of an ester bond to the hydroxy group or an amide bond to the amino group are novel and have improved cell membrane permeability.

5 Claims, 3 Drawing Sheets

PROSTAGLANDIN DERIVATIVES

This application is a continuation of application Ser. No. 793,826, filed Nov. 1, 1985 now abandoned.

BACKGROUND OF INVENTION

The present invention relates to prostaglandin derivatives having cell membrane permeability and a process for preparation thereof.

As is well known, "prostaglandin" (PG) is a generic name of compounds that possess a common skeleton of prostanoic acid of the following formula. They are classified into the groups A, B, C, D, E, F, G/H and I, based on the position of double bond, presence and position of ketone, hydroxy, peroxide and condensed furan ring at the 5-membered ring thereof, and into the groups 1, 2, and 3 based on the number, position and stereochemistry of the double bond in the side chain. They include, for example, $PGA_1$, $PGA_2$, $PGB_1$, $PGB_2$, $PGC_2$, $PGD_2$, $PGE_1$, $PGE_2$, $PGE_3$, $PGF_1\alpha$, $PGF_2\alpha$, $PGF_3\alpha$, $PGG_2$, $PGH_2$, $PGI_2$, etc.

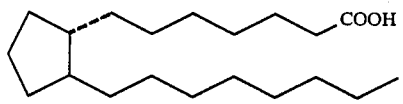

(Formula I)

Prostaglandins exhibit a wide range of physiological activities such as hypotensive activity, diuretic activity, metabolic activity, bronchiectasic activity, uterotonic activity, thyrotropic activity, neuro stimulating activity, gastric juice secretion inhibiting activity, fatty acid release inhibiting activity, etc. Furthermore, in recent years, their carcinostatic activity has attracted special interest. Thus, their uses in pharmaceutical field have been more enhanced.

Since prostaglandins have no substantial permeability to cell membranes and in fact they are usually present outside the cell where they presumably exhibit various pharmacological activities in its original state, no attempt has been made to provide prostaglandins with special permeability to cell membranes.

In the course of the study on the physicochemical and physiological properties of the prostaglandins, it has been surprisingly discovered that when a cell membrane permeable substance having a hydroxy group or an amino group is introduced into carboxy group at 1-position through the intermediation of an ester bond to said hydroxy group or an amide bond to said amino group, the resulting prostaglandin esters or amides show an excellent cell membrane permeability. Although esterification (to methyl ester) and amidation (to dimethylamide) of carboxy group at 1-position of prostaglandin are known, no improvement on cell membrane permeability has been reported with respect to these derivatives. In spite of the fact that the cell membrane permeable substances used in the present invention have a greater bulk than methyl group, it was found that they could impart remarkably improved cell membrane permeability to the prostaglandins when they were combined with prostaglandins through an ester bond or an amide bond as aforedescribed. The prostaglandin esters and amides thus furnished with cell membrane permeability have a greater value than the parent compound because, in addition to the original physiological activity of prostaglandins as such, they show an ability of rapidly exhibiting such physiological activity.

RELATED DISCLOSURES

A comprehensive review on prostaglandins is found in Kirk-Othmer Encyclopedia of Chemical Technology, 3rd. Ed., Suppl. Vol., John Wiley and Sons, N.Y., 1984, Pages 711-752. The above review discloses, for example, $PGG_2$ methyl ester and $PGI_2$ methyl ester.

SUMMARY OF THE INVENTION

According to the present invention, there are provided prostaglandin derivatives having cell membrane permeability characterized in that the carboxy group at 1-position of the prostaglandin is combined with a cell membrane permeable substance having hydroxy group or amino group through the intermediation of an ester bond to said hydroxy group or an amide bond to said amino group. Said derivatives can be prepared by a process which comprises reacting a prostaglandin or a reactive derivative at the carboxy group at 1-position thereof with a cell membrane permeable substance having a hydroxy group or an amine group or a reactive derivative at the hydroxy group or amino group thereof to give a prostaglandin ester or amide.

BRIEF DESCRIPTION OF THE DRAWINGS

The drawings show the permeability properties of prostaglandin derivatives.

DETAILED DESCRIPTION OF THE INVENTION

Figure 4:
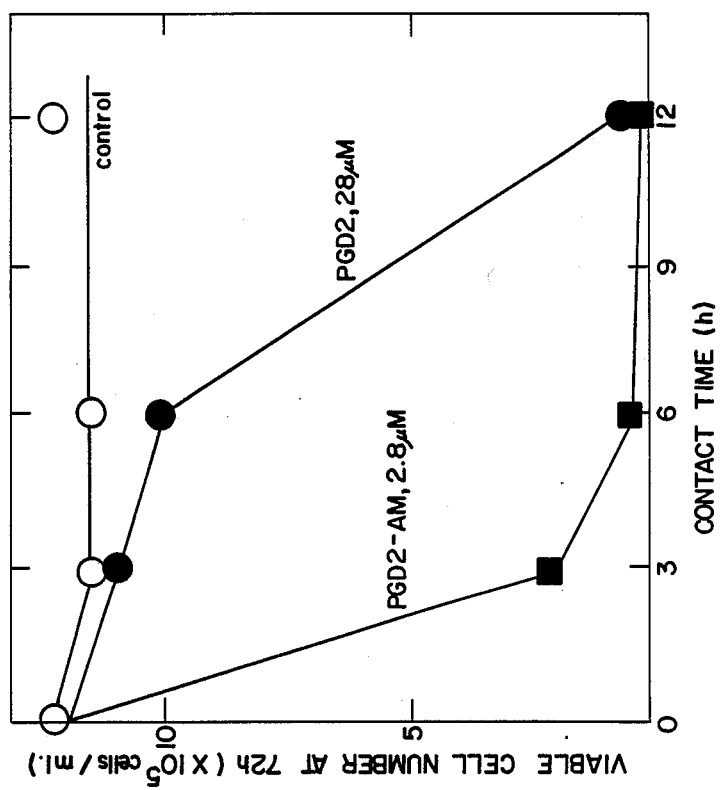

The present invention provides a technique which is generally usable for imparting a cell membrane permeability to prostaglandins. Accordingly, any prostaglandins having at its 1-position a free carboxy group or its reactive derivative group are usable in the present invention.

Specific examples of such prostaglandins are:

1. Prostaglandins such as $PGA_1$, $PGA_2$, $PGB_1$, $PGB_2$, $PGC_2$, $PGD_2$, $PGE_1$, $PGE_2$, $PGE_3$, $PGF_1\alpha$, $PGF_2\alpha$, $PGF_3\alpha$, $PGG_2$, $PGH_2$, $PGI_2$, $\times^{12}$-$PGJ_2$, etc.

2. Prostaglandin analogues such as 9,11-dimethylmethano-11,12-methano-16-phenyl-13,14-dihydro-13-aza-15α$\beta$-ω-tetranor-thromboxan-$A_2$(ONO-11120), 5-(6-carboxyhexyl)-1-(3-cyclohexyl-3-hydroxypropyl)-hydantoin (BW245C), etc.

The hydroxy group-containing cell membrane permeable substance may be one which has per se no specifically notable physiological activity or which is not known to have such activity such as unsaturated aliphatic or alicyclic alcohols or aryl group-containing alcohols. Alternatively, it may be a substance which has per se physiological activity or which is known to have physiological activity such as steroids (e.g., estrogen, etc.) or vitamines. Examples of the hydroxy group-containing cell membrane permeable substance are unsaturated aliphatic or alicyclic alcohols such as citronellol, menthol, borneol, phytol, vitamins $A_1$(retinol), $A_2$, $D_2$, etc., aromatic ring-containing alcohols such as benzyl alcohol, cinnamic alcohol naphthalene-1-methanol, anthracene-9-methanol etc. and steroidal alcohol such as mestanolone, oxandrolone, estradiol monobenzoate, triamcinolone, dexamethasone etc.

The amino group-containing cell membrane permeable substance may be one which has per se no specifically notable physiological activity or which is not known to have such activity. Alternatively, it may be a substance which has per se physiological activity or which is known to have such activity such as vitamins or phenothiazine. Examples of the amino group-containing cell membrane permeable substance are unsaturated aliphatic or alicyclic amines such as geranylamine, mentylamine, bornylamine, phytylamine, 1-aminoadamantane etc., aromatic ring-containing amine such as phenethylamine, 2-naphtylamine, 1-aminoanthracene 9-aminoacridine, vitamins $K_5$, $K_6$, $K_7$, phenothiazine, etc.

These cell membrane permeable substances are generally lipophilic substances of preferably 7 to 25 carbon atoms, which have, in addition to the hydroxyl group or amino group to be used for combining with prostaglandin, at least one unsaturated bond, ring form portion, nitrogen atom, oxygen atom, or sulfur atom and have not an ionic (e.g. carboxylic or sulfonic) group or are not polyfunctional.

Further, such cell membrane permeable substances may be one in which the hydroxyl group or amino group thereof is converted into a reactive derivative. The said reactive derivative may contain appropriate spacer which does not remarkably deteriorate membrane permeability.

The desired prostaglandin esters and amides are obtainable by reacting the above two substances, i.e., prostaglandin and cell membrane permeable substance by the esterification means and amidation means which are conventional per se. Although there is no specific limitation to the esterifsicatrion and amidation means, it is desirable for the reaction to be practiced under mild conditions in order to avoid decomposition of the prostaglandin or cell membrane permeable substance as the starting materials. Typical instance of the mild esterification means conforming to this object includes a so-called diazomethane process. For example, for esterification of prostaglandin with anthracene-9-methanol, anthryl-diazomethane (as a reactive derivative) in which diazo group is introduced instead of hydroxyl group is favorably used. By simply mixing it with prostaglandin in a solvent, esterification is completed at room temperature.

The above esterification and amidation reactions may be carried out by using a suitable coupling reagent (dehydrating agent). For example, in the esterification with retinol, reaction of a well known general coupling reagent for peptide synthesis such as dicyclohexylcarbodiimide, isobutyl chloroformate, pivaloyl chloride, N,N'-carbonyldiimidazol, etc. with prostaglandin according to an ordinary process can give the desired ester or amide in a high yield.

Further, a functional group (amino group or hydroxyl group) of said cell membrane permeable substance may be converted into halogen (a reactive derivative) by an appropriate method and reacted with prostaglandin in the presence of $Ag_2O$ or a tertiary amine to give the desired ester. For the mild amidation reaction, however, the method of using the coupling agent is more effectively employed.

Yet further, for combining a functional group (i.e. amino group or hydroxy group) of said cell membrane permeable substance with prostaglandin combined through an intermediary reactive spacer, retinol, for example, is reacted with bromoacetyl bromide under suitable conditions to give retinol bromoacetate (a reactive derivative), which is then reacted with prostaglandin in the presence of $Ag_2O$ to give the desired derivative of prostaglandin and retinol linked with an ester bond.

Alternatively, phenothiazine and paranitrobenzoic acid is subjected to dehydration to give N-(p-nitrobenzoyl)phenothiazine, which, after reduction, is reacted with prostaglandin to form amide bondage or is diazotized and reacted with prostaglandin and thus affording the desired derivative of prostaglandin and phenothiazine combined through an intermediary amide-amide bond or amide-ester bond. Further, the desired derivative can be prepared by the ester exchange reaction between an active ester (a reactive derivative) of prostaglandin, such as methyl ester or 2,2,2-trichloroethyl ester, and a cell membrane permeable substance.

The obtained prostaglandin ester and amide have generally favorable cell membrane permeability on the one hand and retain physiological activity originated from the prostaglandin starting material on the other hand. When the cell membrane permeable substance used has physiological activities, the product also hold the physiological activities. Accordingly, in addition to rapid onset of physiological activities of prostaglandins, the product show in some cases both the physiological activities of prostaglandins and cell membrane permeable substance synergistically exhibited. It is to be understood that, when used in this specification, the cell membrane permeability include that of blood brain barrier.

Practical and preferred embodiments of the present invention are shown in further detail in the following examples.

EXAMPLE 1

Preparation of PG 9-anthryl methyl ester

A solution of $PGD_2$ or $PGF_{2\alpha}$ or $\Delta^{12}$-$PGJ_2$ in ethanol (100 μg/ml) and a 0.5% solution of 9-anthryl diazomethane in ethyl acetate were mixed together in equal quantities, and the mixture was incubated at 37° C. for 30 minutes. After the reaction was completed, the mixture was concentrated to dryness under nitrogen stream. The product was dissolved in ether or n-hexane and adsorbed on SepPak silica cartridge. $PGD_2$ 9-anthryl methyl ester ($PGD_2$-AM) and $\Delta^{12}$-$PGJ_2$ 9-anthryl methyl ester ($\Delta^{12}$-$PGJ_2$-AM) could be eluted with ethyl acetate and $PGF_{2\alpha}$ 9-anthryl methyl ester ($PGF_{2\alpha}$-AM) with ethanol, respectively. These esters were then purified by reverse phase high performance liquid chromatography. The column was filled with $Cosmosil_5C_{18}$ (4.6×150 mm), and elution of $PGD_2$-AM and $PGF_{2\alpha}$-AM were conducted with methanol/water (8/2). At a flow rate of 0.5 ml/min., $PGD_2$-AM was eluted in 74 min. and $PGF_{2\alpha}$-AM in 36 min. $\Delta^{12}$-$PGJ_2$-AM could also be purified with the similar column. In the latter case, the product was eluted with methanol/water (85/15) at a flow rate of 1 ml/min. in 20 minutes. Rf values in the respective silica gel thin layer chromatography were as noted below (the solvent being ethyl acetate/benzene/acetic acid (50/50/2). $PGD_2$-AM, 0.30; $PGF_{2\alpha}$ —AM, 0.12; and $\Delta^{12}$-$PGJ_2$-AM, 0.80. These esters show fluorescence having a peak at 414 nm at an exciting wavelength of 365 nm.

EXAMPLE 2

Preparation of $PGD_2$ retinol ester $PGD_2$ (1 mg, 2.8 μmol) was dissolved in a mixed solution (0.2 ml) of acetonitrile and tetrahydrofuran at a volume ratio of 2:1. To the solution was added 1- cyclohexyl-3-(2-morpholinoethyl)carbodiimide metho-p-toluene sulfonate (8.2 mg, 39 μmol) and the mixture was stirred at room temperature for 3 minutes. A pyridine solution (0.02 ml) containing retinol (1.4 mg, 4.9 μmol) was added to this mixture, and the mixture was reacted at room temperature for 5 hours. After the reaction was completed, the solvent and pyridine were removed in vacuo and the residue was dissolved in acetone. The product was separated by TLC (fixed phase, silica gel; eluent, chloroform). The structure of the produced PG retinol ester was confirmed by $^1$HNMR.

$^1$HNMR (CDCl$_3$): δ 0.9 (t, 3H), 1.0 (s, 6H), 1.1-2.2 (m, 17H), 1.9-2.3 (m, 7H), 1.7 (s, 3H), 1.85 (s, 3H), 1.96 (s, 3H), 3.5 (m, 2H), 3-4 (b, 2H), 4.1-4.2 (m, 2H), 4.8 (d, 2H), 5.3-6.7 (d, 10H).

EXAMPLE 3

Preparation of PGD$_2$ Phenothiazine amide

Triethylamine (1.0 mg) and isobutyl chloroformate (0.76 mg, 5.6 μmol) were added to a dry acetone solution (0.2 ml) containing PGD$_2$ (1 mg, 2.8 μmol) which was maintained at −10° C. under nitrogen stream. After 3 minutes, an acetone solution (0.1 ml) containing phenothiazine (1.1 mg, 5.6 μmol) was added and the mixture was stirred overnight at room temperature. The reaction solution was concentrated to dryness under reduced pressure and the residue was dissolved in acetone. The product (about 0.7 mg) was separated by TLC in the same manner as in Example 2.

The produced PG phenothiazine amide was identified by $^1$HNMR.

$^1$HNMR (CDCl$_3$): δ 0.9 (t, 3H), 1.1-1.9 (m, 11H), 1.9-2.3 (m, 7H), 3.5 (dd, 2H), 3-4 (b, 2H), 5.3-5.6 (m, 4H), 7.0-8.0 (m, 8H, aromatic H).

EXAMPLE 4

Preparation of PGD$_2$ hydroxyacetyl-retinol ester

According to the conventional method, retinol and bromoacetyl bromide was reacted to produce bromoacetic acid retinol ester.

Bromoacetic acid retinol ester (1.5 mg, 4.0 μmol) and PGD$_2$ (1 mg, 2.8 μmol) were dissolved in methanol (0.5 mg) and the solution was stirred at 0° C. for 24 hours. Thereafter, the solution was post-treated in the same manner as in Example 2 and the product was isolated which was the desired PGD$_2$ hydroxyacetyl-retinol ester (0.6 mg).

$^1$NMR (CDCl$_3$): δ 0.9 (t, 3H), 1.0 (s, 6H), 1.1-2.0 (m, 17H), 1.9-2.3 (m, 7H), 1.7 (s, 3H), 1.85 (s, 3H), 1.96 (s, 3H), 3.5 (m, 2H), 3-4 (b, 2H), 4.1-4.2 (m, 2H), 5.0 (s, 2H), 4.8 (d, 2H), 5.3-6.7 (d, 10H).

EXAMPLE 5

Physiological activity of prostaglandin D$_2$ anthryl methyl ester (PGD$_2$-AM)

(1) Cell membrane permeability

Method

In order to examine cell membrane permeability of PG-AM, PGD$_2$-AM was taken as an example to prepare [$^3$H]PGD$_2$-AM. It was incubated with mouse leukemia cell L-1210 cell at 37° C. After a predetermined time, the cell suspension was aliquoted and washed well with buffer, and then the cells were collected by centrifugation. The radioactivity bound therewith was determined showing the amount of PGD$_2$-AM taken into the cell. For control, [$^3$H]PGD$_2$ having the equal specific activity was used.

Further, in order to verify that the radioactivity combined with cell as observed in the above method was actually taken into the cell, a certain amount of the above suspension was taken on a slide glass, which was sealed with a cover glass, and then observed on a fluorescent microscope.

Results

Figure 1:
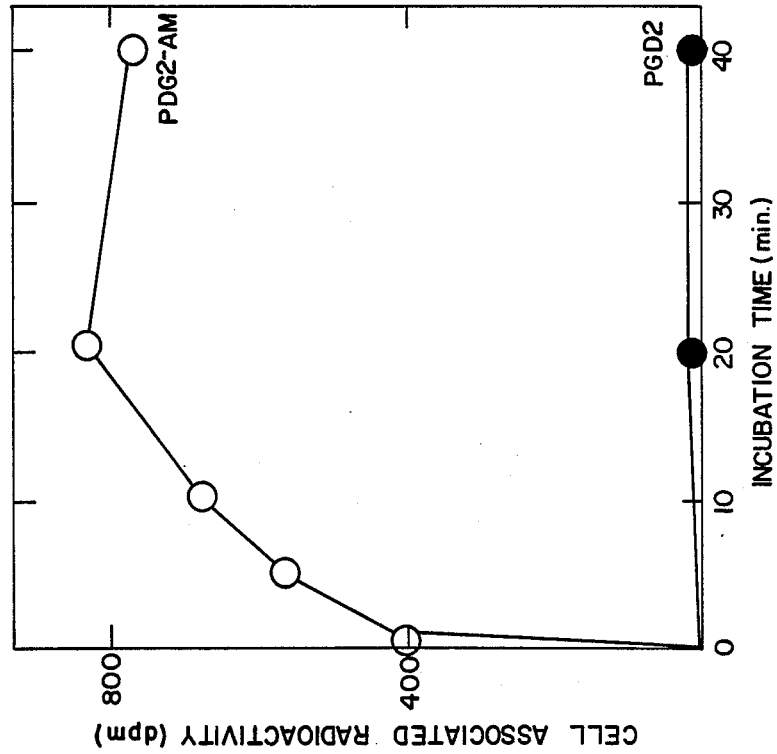
Figure 2:
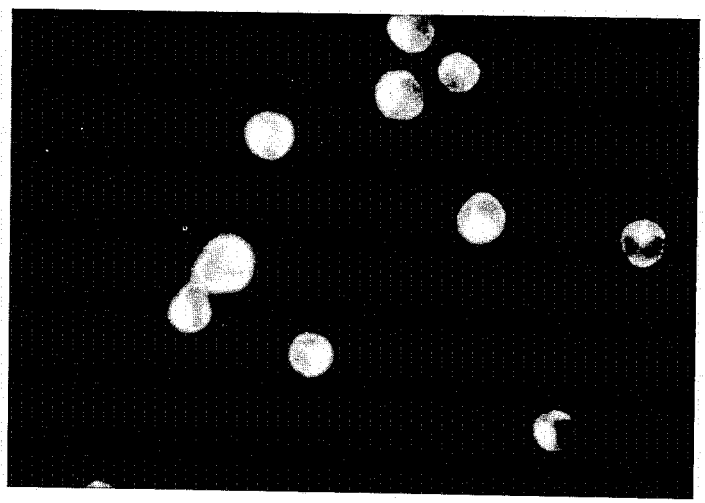

Different from PGD$_2$, PGD$_2$-AM was readily taken into cells and accumulated in cell texture. FIG. 1 shows the change with passage of time for taking into cell. Compared with PGD$_2$ per se having the free carboxylic group, PGD$_2$-AM ester was significantly absorbed into cells as the time proceeds. FIG. 2 shows a microscopic observation of the localization of the taken-in ester, said observation being made in utilization of the fluorescence originated from anthracene portion. From the fact that the fluorescence originated from ester is seen in the cell texture portion, it can be concluded that the ester has been accumulated in said portion.

(2) Intensification of anticancer activity

Method

Figure 3:
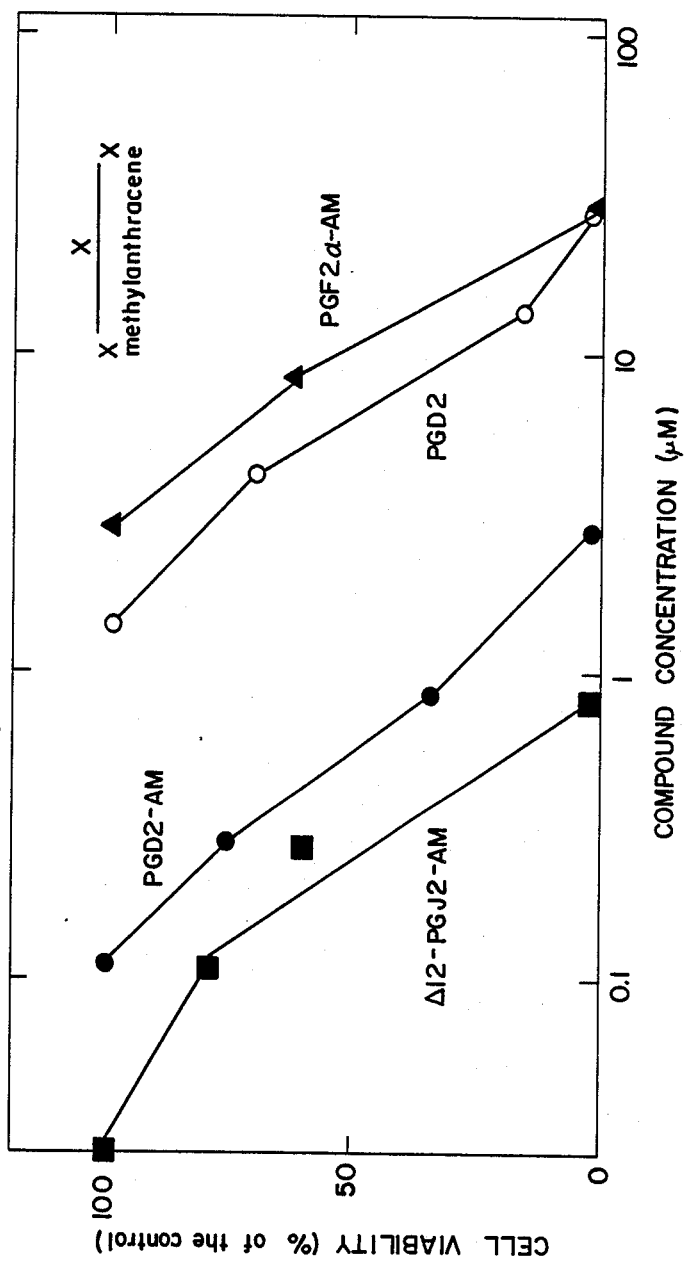

In order to inspect whether or not PG-AM ester preserves inhibiting activity for cancer cell proliferation as observed in free PG, the three compounds, i.e., PGD$_2$-AM, PGF$_{2\alpha}$-AM, and $\Delta^{12}$-PGJ$_2$-AM, were added to L-1210 cell culture in varied concentrations, and their effects upon the proliferating rates were observed. L-1210 cells were inoculated in a density of 10$^5$ cells/ml. After adding PG-AM thereto, the cells were cultivated at 37° C. under 5% CO$_2$ conditions. Seventy-two hours later, the numbers of cells were compared between the culture without addition of PG-AM and those with addition of these esters. FIG. 3 indicates the data taking those for the culture without PG as 100%.

Also, in order to investigate as to whether or not the fact that PG-AM ester was taken into the cells is related with the onset of action, the PG was first added to the cell as above and then washed out after a predetermined time (3, 6 or 12 hours). Thereafter, the cells were returned to the normal liquid culture medium and the effect was judged 72 hours later.

Results

By converting into the anthryl methyl ester, the effect of inhibiting proliferation of cancer cells was increased to more than tenfold, and yet the contact time for onset of the effect could be markedly shortened. FIG. 3 shows the intensified effect. The minimum amount at which proliferation of mouse L-1210 leukemia cells could be fully inhibited was decreased to 2.8 μM in PGD$_2$-AM ester, as compared with 28 μM in PGD$_2$. That is to say, ten-fold intensification of titer was seen.

Also, as seen in FIG. 3, when the effects of the three compounds, i.e., PGD$_2$-AM, PGF$_{2\alpha}$-AM, and $\Delta^{12}$-PGJ$_2$-AM, are compared with one another, $\Delta^{12}$-PGJ$_2$-AM showed the largest effect, followed by PGD$_2$-AM, and then PGF$_{2\alpha}$-AM. Since both $\Delta^{12}$-PGJ$_2$-AM and PGF$_{2\alpha}$-AM showed ten-fold intensification of effect in comparison with $\Delta^{12}$-PGJ$_2$ and PGF$_{2\alpha}$, respectively, it can be concluded from these result that ten-fold stronger effect is obtained in all cases without changing the relative effect between PG's as a result of the esterification. Also, as seen in this graph, there is observed no effect of inhibiting proliferation of cells at all with methyl anthracene per se used as a carrier for membrane permeability.

FIG. 4 shows a comparison between $PGD_2$ and $PGD_2$-AM with respect to the contact time between the compounds and cancer cells necessary for making the inhibition of proliferation irreversible. Compared with the fact that $PGD_2$ requires a contact time of about 12 hours until manifestation of the irreversible activity, $PGD_2$-AM is effective for largely shortening this contact time to 3 hours.

What is claimed is:

1. A compound selected from the group consisting of (a) an ester of a prostaglandin with an alcohol selected from the group consisting of retinol and hydroxyacetylretinol, and (b) prostaglandin phenothiazine amide; the prostaglandin of the prostaglandin ester and the prostaglandin of the prostaglandin phenothiazine amide, each being selected from the group consisting of $PGA_1$, $PGA_2$, $PGB_1$, $PGB_2$, $PGC_2$, $PGD_2$, $PGE_1$, $PGE_2$, $PGE_3$, $PGF_{1\alpha}$, $PGF_{2\alpha}$, $PGF_{3\alpha}$, $PGG_2$, $PGH_2$, $PGI_2$, $\Delta^{12}$-$PGJ_2$, 9,11-dimethylmethano-11,12-methano-16-phenyl-13,14-dihydro-13-aza-15$\alpha\beta$-$\omega$-tetranorthromboxan-$A_2$(ONO-1120), and 5-(6-carboxyhexyl)-1-(3-cyclohexyl-3-hydroxypropyl-hydantoin(BW245C).

2. A prostaglandin derivative as claimed in claim 1 which is $PGD_2$ retinol ester, or $PGD_2$ hydroxyacetylretinol ester.

3. A prostaglandin derivative as claimed in claim 1 which is $PGD_2$ phenothiazine amide.

4. A method of treating a subject with a disease ameliorated by hypotensive activity, diuretic activity, metabolic activity, bronchiectasic activity, uterotonic activity, thyrotropic activity, neuro stimulating activity, gastric juice secretion inhibiting activity, fatty acid release inhibiting activity and carcinostatic activity, said method comprising administering an effective dose of an ester of a prostaglandin with an alcohol selected from the group consisting of retinol, hydroxyacetylretinol and anthracene-9-methanol or prostaglandin phenothiazine amide; the prostaglandin of the prostaglandin ester and the prostaglandin of the prostaglandin phenothiazine amide, each being selected from the group consisting of $PGA_1$, $PGA_2$, $PGB_1$, $PGB_2$, $PGC_2$, $PGD_2$, $PGE_1$, $PGE_2$, $PGE_3$, $PGF_{1\alpha}$, $PGF_{2\alpha}$, $PGF_{3\alpha}$, $PGG_2$, $PGH_2$, $PGI_2$, $\Delta^{12}$-$PGJ_2$, 9,11-dimethylmethano-11,12-methano-16-phenyl-13,14-dihydro-13-aza-15$\alpha\beta$-$\omega$-tetranor-thromboxan-$A_2$(ONO-1120), and 5-(6-carboxyhexyl)-1-(3-cyclohexyl-3-hydroxypropyl-hydantoin(BW245C).

5. A method of providing enhanced permeation of a prostaglandin into cells, said method comprising introducing into said cells ester of said prostaglandin with an alcohol being selected from the group consisting of retinol, hydroxyacetylretinol and anthracene-9-methanol or phenothiazine amide of said prostaglandin; said prostaglandin being selected from the group consisting of $PGA_1$, $PGA_2$, $PGB_1$, $PGB_2$, $PGC_2$, $PGD_2$, $PGE_1$, $PGE_2$, $PGE_3$, $PGF_{1\alpha}$, $PGF_{2\alpha}$, $PGF_{3\alpha}$, $PGG_2$, $PGH_2$, $PGI_2$, $\Delta^{12}$-$PGJ_2$, 9,11-dimethylmethano-11,12-methano-16-phenyl-13,14-dihydro-13-aza-15$\alpha\beta$-$\omega$-tetranor-thromboxan-$A_2$(ONO-1120), and 5-(6-carboxyhexyl)-1-(3-cyclohexyl-3-hydroxypropyl-hydantoin(BW245C).

* * * * *

UNITED STATES PATENT AND TRADEMARK OFFICE
CERTIFICATE OF CORRECTION

PATENT NO. : 4,812,457

DATED : March 14, 1989

INVENTOR(S) : Shuh Narumiya et al

It is certified that error appears in the above-identified patent and that said Letters Patent is hereby corrected as shown below:

On the cover page, the first listed assignee should be --Research Development Corporation of Japan--.

In the first line of the ABSTRACT, change "Permeability" to --Prostaglandin derivatives having cell membrane permeability--.

Signed and Sealed this

Twenty-eighth Day of November 1989

*Attest:*

JEFFREY M. SAMUELS

*Attesting Officer*     *Acting Commissioner of Patents and Trademarks*

UNITED STATES PATENT AND TRADEMARK OFFICE
CERTIFICATE OF CORRECTION

PATENT NO. : 4,812,457

DATED : March 14, 1989

INVENTOR(S) : SHUH NARUMIYA, ET AL

It is certified that error appears in the above-identified patent and that said Letters Patent is hereby corrected as shown below:

On the cover page, the address of the first listed assignee should be -- Tokyo -- instead of "Osaka" and the address of the second listed assignee should be -- Osaka -- instead of "Tokyo"

Signed and Sealed this
Thirteenth Day of February, 1990

*Attest:*

JEFFREY M. SAMUELS

*Attesting Officer*     *Acting Commissioner of Patents and Trademarks*